United States Patent [19]
Melton, Jr.

[11] Patent Number: 5,313,946
[45] Date of Patent: May 24, 1994

[54] METHOD AND APPARATUS FOR THE CHARACTERIZATION OF TISSUE OR OTHER STRUCTURE

[75] Inventor: Hewlett E. Melton, Jr., Sunnyvale, Calif.

[73] Assignee: Hewlett-Packard Company, Palo Alto, Calif.

[21] Appl. No.: 639,486

[22] Filed: Jan. 9, 1991

[51] Int. Cl.$^5$ .............................................. A61B 8/00
[52] U.S. Cl. ............................ 128/660.02; 73/861.25
[58] Field of Search ...................... 128/660.02, 661.08, 128/661.09, 696, 715; 73/861.25

[56] References Cited

U.S. PATENT DOCUMENTS

| | | | |
|---|---|---|---|
| 4,038,536 | 7/1977 | Feintuch | 128/696 |
| 4,800,891 | 1/1989 | Kim | 128/661.09 |
| 5,036,857 | 8/1991 | Semmlow et al. | 128/715 |
| 5,052,395 | 10/1991 | Burton et al. | 128/661.08 |

Primary Examiner—Francis Jaworski
Assistant Examiner—George Manuel

[57] ABSTRACT

A method and apparatus are provided for determining correlation length of body tissue, metals, crystals, or other materials, substances and the like having an ordered internal stucture (hereinafter structures) and for utilizing such correlation length to test, classify or otherwise characterize the structure. The structure is scanned using standard ultrasonic scanning technology and the output from such scan is processed to determine correlation length in one dimension (length), two dimensions (area), three dimensions (volume). A fourth dimension of time may also be used with one or more of the other three dimensions in the correlation length determination.

20 Claims, 1 Drawing Sheet

METHOD AND APPARATUS FOR THE CHARACTERIZATION OF TISSUE OR OTHER STRUCTURE

FIELD OF THE INVENTION

This invention relates to nondestructive testing and classification and more particularly to a method and apparatus for utilizing the output signals from an ultrasonic scanner to determine the correlation length of a tissue or other material or structure to be tested or classified, such correlation length being a generally unique characteristic which may be utilized to classify a structure and thereby to define certain characteristics thereof.

BACKGROUND OF THE INVENTION

There are a number of fields in which improved noninvasive and nondestructive testing and characterization techniques are required. In the field of medicine, various noninvasive testing techniques currently exist, such as ultrasonic scanning and x-rays, which produce images of bone or tissue. Such images are useful for detecting abnormalities in size or shape of an organ, for detecting blockages or other abnormalities in arteries or for detecting fractures in bones. However, such images generally do not reveal chemical or other structural changes in tissue or bone which may be useful in the early diagnosis of various medical problems. For example, a change in bone structure might be indicative of the onset of osteoporosis, while changes in the organization of certain cells within an organ might be an early indication of cancer. Other organ diseases, including those of the heart, lung, liver and kidney, might also result in organizational changes in all or a portion of the affected organ which, if detected, could be used for diagnostic purposes. Further, since a noninvasive procedure such as ultrasonic scanning which does not involve any known risk or substantial discomfort to the patient may be performed at frequent intervals, such a technique could also be utilized to determine the effectiveness of various treatment regimens so that such regimens may be adjusted to meet the needs of the patient.

Similarly, with the aging infastructure in the United States and other countries, aging airline fleets and the like, there is an increasing need for a capability to nondestructively test structures, composite materials and equipment before problems develop. Again, various techniques are currently available which can detect cracks, breaks, bends or similar abnormalities which would turn up when an image of a structure, including hidden structures, is produced. However, problems in such structures can also arise as a result of oxidation, structural fatigue, or other compositional or structural changes which may occur as a result of time, use, shocks or corrosion which might not show up in an image of the structure.

SUMMARY OF THE INVENTION

In accordance with the teachings of this invention, it has been found that correlation length is a unique characteristic of materials, substances, etc. having ordered internal structures such as those within human tissue or various crystals. The structure may be scanned using standard ultrasonic scanning equipment and technology. By scanning, for example, tissue which is known to be healthy norms can be established for various types of tissue. Similarly, norms can be established for other structures such as crystals. With such norms established for normal and/or abnormal structures, it is possible by scanning the structure to be categorized with an ultrasonic scanner, and processing the output from the ultrasonic scanner to determine the correlation length for the structure, to determine if the structure is normal or abnormal. Such determination may be a simple binary determination wherein a threshold is established, with readings on one side of the threshold being considered normal and readings on the other side of the threshold abnormal. More detailed determinations may be made from the varying correlation lengths of the structures.

The correlation lengths of human tissue may also change with age. Similar changes may also occur in other cellular structures. Thus, correlation length may also be usable, by establishing suitable norms, for dating unknown items or for other similar purposes.

Correlation length is obtained by mathematically manipulating a covariance function of the ultrasonic scanner output. It is preferable that the auto covariance be utilized for this purpose. The covariance function, and thus the correlation length, may be determined in a single dimension as length, in two dimensions as an area, in three dimensions as a volume, or in one or more of the three dimensions plus time. For one dimension, the determination is made on a single ultrasonic beam. For two dimensions, the determination is made on a succession of ultrasonic beams as the beam is swept across the tissue or other structure. For three dimensions, in addition to the beam sweep, the scanner may also be moved in known ways in a direction perpendicular to the sweep to provide three dimensional information. By providing successive sweeps of the same line, area or volume, changes with time can also be noted, thus adding a potential fourth dimension. An equation for determining correlation length in general is presented in the material to follow as is a specific circuit for implementing the determination of correlation length.

The foregoing and other objects, features and advantages of the invention will be apparent from the following more particular description of a preferred embodiment of the invention as illustrated in the accompanying drawings:

IN THE DRAWINGS

DETAILED DESCRIPTION

Figure 1:
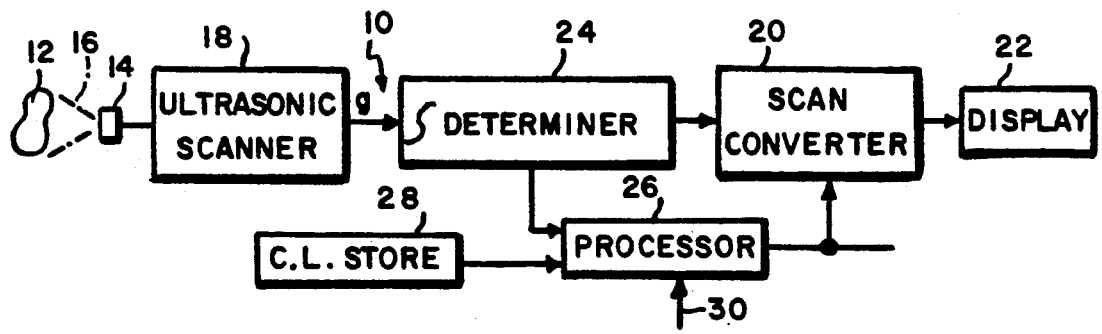
FIG. 1 is a semi-block schematic diagram of a system in which the teachings of this invention may be practiced.

FIG. 1 illustrates a system 10 which may be utilized to characterize a structure 12 by use of correlation length. The system may also be utilized to display correlation lengths in one, two or three dimensions in a predetermined format and to make certain determinations from the computed correlation lengths for structure 12 to, for example, identify the structure or determine if any abnormalities exist in the structure. The system ma also be utilized for localizing abnormalities in a given structure and may, in some instances, also be useful in dating a structure.

The structure 12 may, for example, be a human or animal organ such as a heart, liver, kidney, or the like, some other tissue structure of a body, or some type of crystal or other material such as a metal or other material being used in a construction or manufacturing application.

The structure 12 is scanned by a standard ultrasonic scan head 14 which may, for example, be an electronic phased array scan head or a mechanically rotating scan head. Signals to drive scan head 14 to project an ultrasonic beam 16 at structure 12 are obtained from a standard ultrasonic scanner system 18 and echoes picked up by head 14 from structure 12 are applied to scanner system 18.

Figure 4:
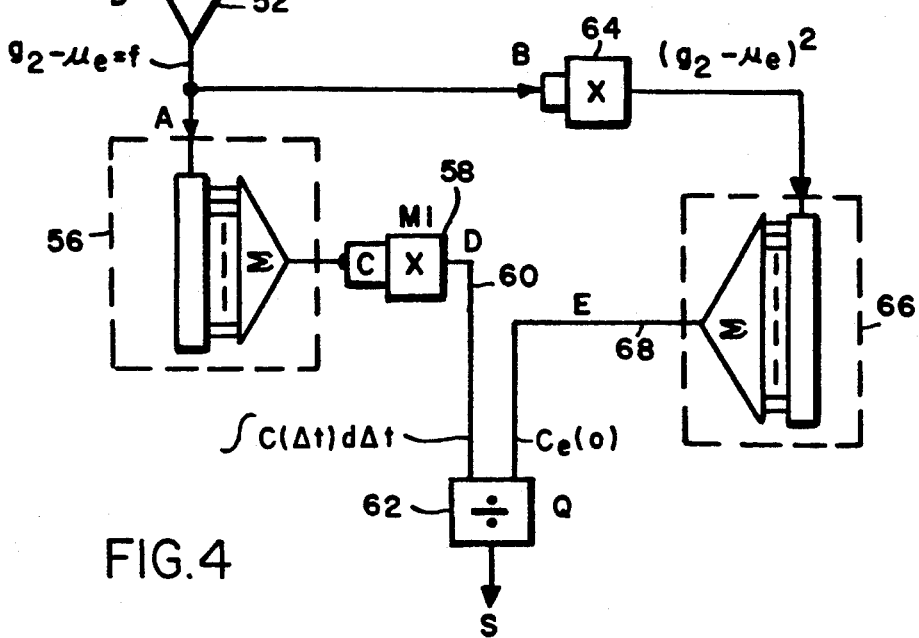
FIG. 4 is a schematic diagram of a circuit which might be utilized as the correlation length determiner in the circuit of FIG. 1.

In a standard system, the output signal "g" from the ultrasonic scanner 18 is utilized to drive a scan converter 20 which, in turn, causes an image of the structure 12 being scanned to appear on a display 22. Display 22 would typically be a standard cathode ray tube display monitor. In accordance with the teachings of this invention, an additional device 24 is inserted in the system between scanner 18 and scan converter 20 to make the correlation length (S) determination for the structure. While in the discussion to follow it will be assumed that device 24 is implemented in hardware as shown in FIG. 4, and this may be the fastest implementation, it is to be understood that the determination of correlation length "S" could also be done by programming a processor used elsewhere in the system to perform this function, may be a mircroprocessor used solely for this function, or may be a processor operating with a microcode ROM. The last implementation may be the preferred embodiment, effecting a reasonable compromise between cost and speed of operation.

Figure 3:
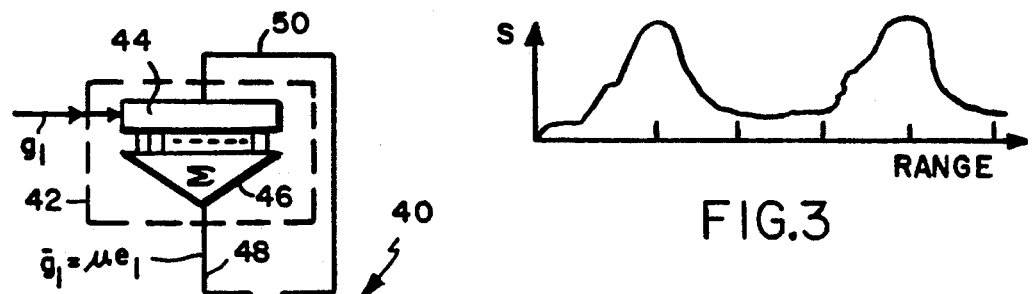
FIG. 3 is a diagram illustrating an exemplary correlation length.

The correlation length determined by element 24 may be applied to scan converter 20, causing a display of correlation length in an appropriate format to appear on display 22. The format for the display may, for example, be graphic, as shown in FIG. 3, may be alphanumeric, or may be indicated as a change in brightness, color or the like for the structure under test or a part thereof, depending on the length at the given point.

The correlation output from element 24 may also be applied as one input to a processor 26, the other input to this processor being from a correlation length storage device 28. Processor 26 may be a general purpose microprocessor, some type of special purpose circuit which may receive an input over line 30 indicating a type of structure being scanned or a processor used for other functions which is also suitably programmed to perform this function. Store 28 may contain normal correlation lengths or normal correlation length ranges for various structures, for example, for various human organs where the system is being utilized for medical diagnosis, and may also contain indications of various types of abnormalities which may be indicated for a particular type of tissue with different correlation lengths or length ranges. Alternatively, a threshold value may be stored for a given tissue or organ with correlation lengths on one side of the threshold being considered normal and correlation lengths on the other side of the threshold being considered abnormal for a given type of tissue. When the system is being used for other applications, similar information might be stored for other appropriate types of structures.

Processor 26 retrieves appropriate correlation length information for the structure 12 under test from store 28, compares current inputs from element 24 against the retrieved correlation length values, and generates an appropriate output to indicate whether the structure under analysis is normal or abnormal and, under proper circumstances, the nature of the abnormality. Abnormality may exist for the entire structure under analysis, for example, for a liver or kidney, or may be localized in a particular region of the organ as, for example, with cancer.

The output from processor 26 is applied to scan converter 20 and may be utilized to cause a display either in addition to or instead of the display caused by the output from element 24. Again, the information may be conveyed in graphic or alphanumeric form or may be reflected by changing the color, intensity or the like on the image of the structure being generated on display 22 to reflect a particular abnormality and possibly to reflect the region of the organ or the like where abnormality exists.

Figure 2:
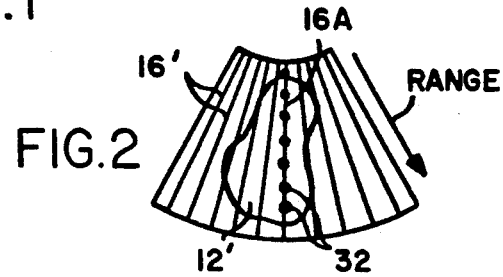
FIG. 2 is a diagram illustrating the scanning of a structure to be characterized.

FIG. 2 illustrates the scanning of the structure 12, FIG. 2 basically being an image 12' of the structure as it might appear on display 22. Scan head 14 is adapted to successively generate a plurality of ultrasonic scanning beams which are illustrated as the beams 16' in FIG. 2. As illustrated for the beam 16A, each line has a plurality of points 32 thereon at which correlation length determinations may be made. For example, there may be 100 to 200 scan lines 16' during a given scan with approximately 500 points 32 at which correlation length determinations are made for each of the lines 16'.

A single scan line 16 (or 16'), with correlation length being determined at each point 32 therealong, provides a one dimensional indication of correlation length for the structure 12. Determining correlation length using all the scan lines 16 gives a two dimensional correlation area for the structure. Moving scan head 14 o scan successive sections of structure 12 provides a three dimensional indication of correlation volume. The fourth dimension of time may be added by repeating a one, two or three dimensional scan at successive time intervals. The values (S) determined at each point 32 may be stored and used to generate a correlation length indication for such point, or the values at each point may be summed or otherwise combined in a predetermine way to obtain a correlation length value (or values) which may be used for comparison or other purposes.

FIG. 3 illustrates what correlation length S represents. FIG. 3 is a graph of correlation length (S) versus range (distance) along the scan line 16A shown in FIG. 2. The value of (S) goes u in regions of the scanned structure where the scale of organization in the structure is measurably larger; the value of (S) goes down in those regions where the scale of organization is measurably smaller. These changes in S along any one scan line, and in particular along line 16A as illustrated portray the variation in the measurable scale of organization within the scanned structure. The lower limits on the measurable scale of organization are dictated by the wavelength of the ultrasonic beam being utilized and to some extent by the focus of the beam. Thus, to the extent it is desired to measure correlation length with finer resolution on scale of organization, a higher frequency, shorter wavelength ultrasonic scanning beam must be utilized. Such measurable variations in correlation length and the localization of these variations within the field of view provided by all the scan lines, 16, can render in image or numeric form indications of defects, abnormalities, variations in composition, in strain, in density, in velocity of propogation, in velocity of motion, in elasticity and in the order within the scanned structure.

FIG. 4 shows a circuit which might be utilized as the circuit 24 to generate correlation length at each sample point 32. The circuit of FIG. 4 basically implements the following equation for correlation length S:

$$S = \frac{\int_{-\infty}^{\infty} C(\Delta\chi) d(\Delta\chi)}{C(o)}$$

where:

$$C(\Delta\chi) = \int_{-\infty}^{\infty} f(\chi)f(\chi + \Delta\chi)d\chi$$

$$C(o) = \int_{-\infty}^{\infty} [f(\chi)]^2$$

$f(\chi) = g(\chi) - \overline{g(\chi)}$
$g(\chi)$ = the output signal from scanner 18
$\overline{g(\chi)}$ = the average $g(\chi)$ over a selected length interval In the above equation $C(\Delta\chi)$, represents the covariance function, this function being the autocorrelation function for the preferred embodiment.

In particular, the input to the circuit 40 is the $g_1$ signal output from ultrasonic scanner 18. This signal is fed to a finite impulse response filter 42. Filter 42 consists of a sampler or tapped analog delay line 44 which stores the values for a predetermined number of successive sample points 32, and a summing circuit 46 to which the values stored in delay line 44 are applied.

The summing circuit 46 also functions to divide the summed value by the number of inputs so that the output from circuit 42 on line 48 is the average value ($g_1$) of the $g_1$ values stored in delay line 44. A variable tap is used to obtain a value $g_2$ on line 50 which is a delayed version of $g_1$. The delay can vary from zero to the maximum delay with the exact value of this delay not being critical.

The moving estimate of value on line 48 and the delayed value on line 50 are applied as the two inputs to a difference circuit 52 which functions to subtract the value on line 48 from the value on line 50. From the equations previously provided, it is seen that the output on line 54 from difference circuit 52 is the value "f". The f signal on line 54 is applied through two channels. The first channel includes a finite impulse response filter 56 which functions to integrate the f signal. The output from circuit 56 is then applied as both inputs to a multiplier circuit 58. The resulting output on line 60 is a taper weighted version of the $\int C(\Delta\chi) d\Delta\chi$ function of the prior equations and is written here as $\int C_w(\Delta t) d\Delta t$. This value is applied as the numerator input to divider circuit 62.

The signal on line 54 is also applied as both inputs to a multiplier circuit 64 which functions to perform an $f^2$ function. The $f^2$ output from circuit 64 is applied to finite impulse response filter 66 which effectively integrates the output from circuit 64, resulting in a signal on line 68 which is equal to the C(o) function of the prior equations and is written here as $C_e(o)$ The signal on line 68 is applied as the denominator input t divider circuit 62. The output from divider circuit 62 gives a measure for correlation length (S).

The value (S) for a known structure may, for example, be stored in store 28 while the value (S) for unknown structures may be applied to processor 26 for analysis and classification.

A system has thus been provided which permits tissue, crystals or other structures or materials to be determined and categorized by determining their correlation length and utilizing such correlation length to effect the desired characterization and differentiation.

While the invention has been particularly shown and described above with reference to a preferred embodiment, it is apparent that the foregoing other changes in form and detail may be made therein by one skilled in the art while still remaining within the spirit and scope of the invention.

What is claimed is:

1. A system for the characterization of a structure comprising:
   means for ultrasonically scanning the structure to be characterized, said scanning means generating output signals corresponding to pulse echo signals received during such scan by the scanning means for selected points in the structure; and
   means responsive to said output signals for determining the correlation length for said structure, said correlation length being measurable characteristic of the structure.

2. A system as claimed in claim 1 wherein the means for determining correlation length utilized a covariance function of said output signal in making said determination.

3. A system as claimed in claim 2 wherein said covariance function is determined in one dimension.

4. A system as claimed in claim 2 wherein said covariance function is determined in two dimensions.

5. A system as claimed in claim 2 wherein said covariance function is determined in three dimensions.

6. A system as claimed in claim 2 wherein said covariance function is determined in at least one space dimension and is also determined in a time dimension.

7. A system as claimed in claim 2 wherein the covariance function is autocovariance.

8. A system as claimed in claim 2 wherein correlation length S is determined using the relation:

$$S = \frac{\int_{-\infty}^{\infty} C(\Delta\chi) d(\Delta\chi)}{C(o)}$$

where:

$$C(\Delta\chi) = \int_{-\infty}^{\infty} f(\chi)f(\chi + \Delta\chi)d\chi$$

$$C(o) = \int_{-\infty}^{\infty} [f(\chi)]^2$$

$f(\chi) = g(\chi) - \overline{g(\chi)}$
$g(\chi)$ = the output signal
$\overline{g(\chi)}$ = the average $g(\chi)$ over a selected length interval.

9. A system as claimed in claim 1 wherein said structure is body tissue.

10. A system as claimed in claim 1 wherein said means for determining includes means for obtaining the average of said output signals over a predetermined time interval:
  means for subtracting a selected output signal from said determined average to obtain a value (f);
  first means for integrating said value (f) and then squaring the integrated value;
  second means for squaring said value (f) and then integrating the squared value; and
  means for dividing the output of said first means by the output of said second means to obtain correlation length.

11. A system as claimed in claim 10 wherein said means for obtaining the average and said means for integrating are impulse response filters.

12. A method for the characterization of a structure comprising the steps of:
  ultrasonically scanning the structure to be characterized, said scanning step generating an output corresponding to pulse echo signals received during such scan by the scanning step for selected points in the structure; and
  utilizing said output to determine the correlation length for said structure, said correlation length being a measurable characteristic of the structure.

13. A method as claimed in claim 12 wherein a covariance function of said output is utilized in making the correlation length determination.

14. A method as claimed in claim 13 wherein said covariance function is determined in one dimension.

15. A method as claimed in claim 13 wherein said covariance function is determined in two dimensions.

16. A method as claimed in claim 13 wherein said covariance function is determined in three dimensions.

17. A method as claimed in claim 13 wherein said covariance function is determined in at least one space dimension and is also determined in a time dimension.

18. A method as claimed in claim 13 wherein the covariance function is autocovariance.

19. A method as claimed in claim 13 wherein correlation length S is determined using the relation:

$$S = \frac{\int_{-\infty}^{\infty} C(\Delta\chi) d(\Delta\chi)}{C(o)}$$

where:

$$C(\Delta\chi) = \int_{-\infty}^{\infty} f(\chi) f(\chi + \Delta\chi) d\chi$$

$$C(o) = \int_{-\infty}^{\infty} [f(\chi)]^2$$

$f(\chi) = g(\chi) - \overline{g(\chi)}$
$g(\chi)$ = the output signal
$\overline{g(\chi)}$ = the average $g(\chi)$ over a selected length interval.

20. A method as claimed in claim 12 wherein said structure is body tissue.

* * * * *